United States Patent [19]  [11] 3,985,562
Mertens et al.  [45] Oct. 12, 1976

[54] DIAZO RECORDING PROCESS AND MATERIAL

[75] Inventors: Ludovicus Maria Mertens, Borgerhout; Gerard Albert Delzenne, 's-Gravenwezel, both of Belgium

[73] Assignee: AGFA-GEVAERT N.V., Mortsel, Belgium

[22] Filed: Oct. 28, 1975

[21] Appl. No.: 626,347

Related U.S. Application Data

[62] Division of Ser. No. 437,763, Jan. 30, 1974, abandoned.

[30] Foreign Application Priority Data

May 18, 1973    United Kingdom............... 23861/73

[52] U.S. Cl............................... 96/49; 96/75.91 D; 96/91 R
[51] Int. Cl.²....................... G03C 5/34; G03C 1/60
[58] Field of Search........ 96/49, 91 R, 91 D, 115 R, 96/75, 114.1

[56] References Cited
UNITED STATES PATENTS

| | | | |
|---|---|---|---|
| 2,727,820 | 12/1955 | Botkin et al. | 96/91 R |
| 2,755,185 | 7/1956 | Sulich et al. | 96/91 R |
| 2,974,042 | 3/1961 | Sus et al. | 96/91 D |
| 3,113,865 | 12/1963 | Sagura et al. | 96/91 R |
| 3,199,982 | 8/1965 | Kashiwabava | 96/91 R |
| 3,255,007 | 6/1966 | Kosav | 96/91 R |
| 3,453,112 | 7/1969 | Schaeffer | 96/91 R |
| 3,493,374 | 2/1970 | Roncken et al. | 96/49 |
| 3,563,744 | 2/1971 | Poot et al. | 96/49 |
| 3,676,140 | 7/1972 | Poot et al. | 96/91 R |
| 3,794,488 | 2/1974 | Herr et al. | 96/114.1 |

FOREIGN PATENTS OR APPLICATIONS

1,128,762   10/1968   United Kingdom................. 96/91 R

OTHER PUBLICATIONS

Noller, C. R., "Textbook of Organic Chemistry," 2nd Ed. W. B. Saunders Co., 1958, pp. 180 and 243.
Kosar, J., "Light–Sensitive Systems," Wiley & Sons, 1965, pp. 219 and 295.

*Primary Examiner*—Charles L. Bowers, Jr.
*Attorney, Agent, or Firm*—William J. Daniel

[57]          ABSTRACT

A diazo recording process which comprises the steps of (1) information-wise exposing to ultra-violet light and (2) overall heating a recording material comprising a compound yielding an amine on heating, an ultra-violet light-sensitive diazo compound and a coupling component capable of yielding a dyestuff by reaction with unaffected diazo compound when heating said material and wherein the compound yielding an amine on heating corresponds with the following general formula:

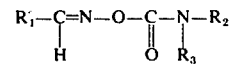

in which:
  $R_1$ represents
    1. an aliphatic group or a cycloaliphatic group,
    2. an aryl group,
    3. a heterocyclic group, or
    4. an acyl group,
  $R_2$ represents an aliphatic group or a cycloaliphatic group,
  $R_3$ represents
    1. hydrogen,
    2. an aliphatic group including a cycloaliphatic group, or
  $R_3$ and $R_2$ form together part of a heterocyclic ring.

17 Claims, No Drawings

# DIAZO RECORDING PROCESS AND MATERIAL

This is a division, of Ser. No. 437,763, filed Jan. 30, 1974, now abandoned.

The present invention relates to photosensitive heat-developable compositions and elements comprising such compositions.

The diazo compositions most widely employed in conventional diazo coatings comprise a photodecomposable diazo compound, an organic coupling component and an acid. An element coated with this composition is exposed to ultraviolet light through a negative or positive transparent original and the diazo compound is decomposed only in the areas exposed to light. In the unexposed portions the diazo compound remains unaffected and is subjected to further reaction in the presence of an alkaline reagent to produce a coloured image with the coupler. The alkaline material for promoting the reaction is generally ammonia, applied either as a gas or as a solution. The shifting of the pH of the dye forming system to the alkaline range allows the formation of a dye image.

Light-sensitive papers coated with such compositions have been produced commercially, but the application of a separate alkaline substance, such as ammonia is very unpleasant and poisonous. In addition, relatively complex copying devices are required for use in conjunction with such copying materials since means must be provided for generating the developing fluids and for evacuating the gaseous products.

It is one of the objects of the present invention to overcome the difficulties associated with conventional diazo copying materials.

More specifically, it is an object of the present invention to provide a diazo recording composition which is developable by heat alone and which may be employed in relatively simple copying devices wherein no means for generating developing fluids or evacuating poisonous gaseous products need to be provided.

Another object of this invention is to provide a diazo recording process wherein the azo dye forming reaction is started and promoted by a raise of the pH of the recording composition with an amine that is set free by heating.

The recording material of the present invention comprises a compound yielding an amine on heating, a diazo compound and a coupling component capable of yielding a dyestuff by reaction with said diazo compound when heating said material, wherein the compound yielding an amine on heating corresponds to the following general formula:

$$R_1-\underset{H}{\underset{|}{C}}=N-O-\underset{O}{\underset{\|}{C}}-\underset{R_3}{\underset{|}{N}}-R_2$$

in which:
$R_1$ represents
1. an aliphatic group including a cycloaliphatic group and such groups in substituted form e.g. an alkyl group having a straight carbon chain or branched chain structure including substituted alkyl group e.g. a $C_1-C_{18}$ alkyl group e.g. methyl, ethyl, n-propyl, isopropyl, hexyl, dodecyl, or octadecyl, an alkoxy-substituted alkyl group, an alkoxycarbonyl-substituted alkyl group e.g. a carbethoxymethyl group, an alkenyl group including a substituted alkenyl group e.g. an allyl group, a cycloalkyl group including a substituted cycloalkyl group e.g. cyclopentyl, cyclohexyl, or methylcyclohexyl, an aralkyl group including a substituted aralkyl group e.g. a benzyl group or phenethyl group,
2. an aryl group including a substituted aryl group, e.g. a phenyl group, a naphthyl group or a biphenyl group including these groups in substituted form, e.g. a halogen-substituted phenyl group such as 4-chlorophenyl and 3,4-chlorophenyl, alkyl-substituted phenyl e.g. a tolyl group, hydroxy-substituted phenyl, alkoxy-substituted phenyl, in which the alkyl group of the alkoxy group is e.g. a $C_1-C_{18}$ alkyl group, a carboxy-substituted phenyl, an esterified carboxy-substituted phenyl group e.g. a methoxycarbonyl-substituted phenyl group, a cyano-substituted phenyl group, a fluorosulfonyl-substituted phenyl group or a nitro-phenyl group.
3. a heterocyclic group including a substituted heterocyclic group, or
4. an acyl group e.g. an aliphatic or aromatic acyl group derived from a carboxylic or sulphonic acid e.g. acetyl, methylsulphonyl, benzoyl, or phenylsulphonyl, $R_2$ represents an aliphatic group including a cycloaliphatic group, $R_3$ represents
1. hydrogen or
2. an aliphatic group including a cycloaliphatic group, or $R_3$ and $R_2$ form together part of a heterocyclic ring e.g. a saturated heterocyclic ring such as a piperidine or morpholine ring.

The heat reaction applied in the present invention to set free the amine may be represented by the following reaction scheme:

$$R_1-\underset{H}{\underset{|}{C}}=N-O-\underset{O}{\underset{\|}{C}}-\underset{R_3}{\underset{|}{N}}-R_2 \xrightarrow{heat} CO_2 + H-\underset{R_3}{\underset{|}{N}}-R_2 + R_1-C\equiv N$$

When $R_2$ and/or $R_3$ is (are) an aliphatic or cycloaliphatic group or form part of a ring structure, amines are produced that fairly strongly raise the pH of the medium. This is the case e.g. when saturated heterocyclic compounds e.g. piperidine, morpholine or pyrrolidine are set free thermolytically.

Specific compounds that behave according to said reaction scheme are listed in the following table 1 with their melting point.

Table 1

| Compound | Structural formula | Melting point °C |
|---|---|---|
| 1 | ⌬—CH=N—O—C(=O)—NH—C₄H₉ | oil at 20° C |

Table 1-continued

| Compound | Structural formula | Melting point °C |
|---|---|---|
| 2 | ⟨Ph⟩—CH=NHCON⟨piperidyl⟩ | 136 |
| 3 | ⟨Ph⟩—C(H)=NOC(O)—N⟨morpholino⟩ | 120 |
| 4 | ⟨Ph⟩—C(H)=NOC(O)—N(CH$_2$—CH$_2$—CH$_3$)$_2$ | oil at 20° C |

The compounds used in the present invention may be prepared according to the following two reaction schemes A and B:

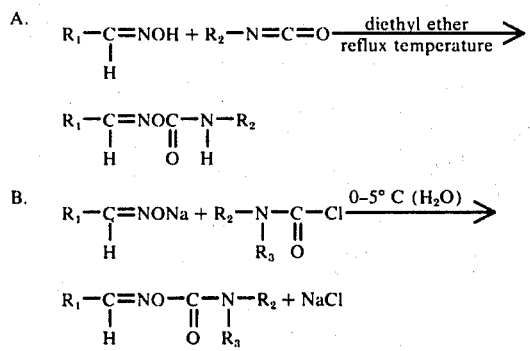

A.
$$R_1-\underset{H}{C}=NOH + R_2-N=C=O \xrightarrow[\text{reflux temperature}]{\text{diethyl ether}}$$

$$R_1-\underset{H}{C}=N-O-\underset{O}{\overset{\|}{C}}-\underset{H}{N}-R_2$$

B.
$$R_1-\underset{H}{C}=NONa + R_2-\underset{R_3}{N}-\underset{O}{\overset{\|}{C}}-Cl \xrightarrow{0-5° C (H_2O)}$$

$$R_1-\underset{H}{C}=N-O-\underset{O}{\overset{\|}{C}}-\underset{R_3}{N}-R_2 + NaCl$$

The listed compounds have been prepared according to the following preparation receipts:

Preparation of compound 1

6 g of benzaloxime were dissolved in 10 ml of diethyl ether and 5 g of butyl isocyanate dissolved in 10 ml of diethyl ether were added thereto. The reaction mixture was boiled with reflux for 2 h. The diethyl ether was removed by evaporation.

Yield of 4 of oily product.

Preparation of compound 2

1.2 g of benzaloxime were dissolved in 5 ml of diethyl ether and 2 ml of triethyl amine were added thereto. To the obtained mixture 1.47 g of piperidyl carbonyl chloride dissolved in 5 ml of diethyl ether were added. The reaction mixture was kept for 1 h at room temperature. The precipitate was sucked off.

Yield: 1.5 g. Melting point: 136° C.

Preparation of compound 3

2.4 g of benzaloxime were added to a solution of 1 g of sodium hydroxide dissolved in 20 ml of water. The reaction flask containing the obtained solution was cooled down with ice water and 3 g of morpholino carbonyl chloride added dropwise thereto. The reaction mixture was stirred for a further period of 1 h.

Yield: 4 g. Melting point: 120° C.

Preparation of compound 4

2.4 g of benzaloxime were dissolved in 10 ml of diethylether and 5 ml of triethyl amine were added thereto. To the obtained mixture 3.2 g of di-propylamine carbonyl chloride dissolved in 30 ml of diethylether were added. The reaction mixture was boiled with reflux for 4 h, thereupon cooled down, filtered and the ether removed by evaporation.

Yield: 5 g of oily product.

The thermosensitive amine progenitors used according to the present invention are stable under conditions normally encountered in the manufacture, storage and shipment of the present recording material. The activation temperature of most of the amine progenitor compounds used is between 40° C and 120° C.

The term diazo compound in the present invention includes a diazonium salt, an aromatic diazo-oxide and a diazo sulphone. A detailed discussion of the first two types of compounds and their behaviour on exposure is presented in the article "The Diazotype Process" by R. Landau, Chemistry and Industry, Mar. 31, (1962) p. 572-575.

Suitable diazonium salts and aromatic coupling compounds are described in "Photographic Chemistry" by P Glafkides (Fountain Press, London), Vol. II, p 716, The Journal of Photographic Science, Vol. 13, (1965) p. 144-151, in the Belgian Patent Specification 682,022 and in Light-Sensitive Systems by Jaromir Kosan — John Wiley & Sons Inc., New York (1965) p. 201-214.

Aromatic diazo-oxide compounds e.g. 2,1-diazo-oxides are further described in Fortschr.Chem.Forsch. 5, 1-88 (1965) by W. Ried and H. Mengler, in Angew. Chem. 11, (1961) 368-371 and in Angew.Chem. 24 (1962) 985-988.

Suitable diazosulphone compounds are described in the United Kingdom Patent Specifications 1,277,029 and 1,277,428.

The amine yielding compounds may be incorporated in or on a support of a 2-component diazo-type recording material. It may be applied onto or into a sheet or layer (this layer either being supported or self-supporting) in any way known in the art of coating techniques and preparation of diazo-type materials, the only requirement being that it be present in operative relationship i.e. is in working contact or can come into reactive contact by heat with the 2-component diazo-type composition, i.e. the diazo compound and coupling agent. The amine producing compound may be combined with ordinary commercial diazo-type copy sheets, which contain both the diazo compound and the coupler as a coating over the amine producing layer. So, according to one embodiment, the thermosensitive amine producing compound is dissolved in a solution of a binder and coated onto the support of the diazo-composition layer as an intermediate layer.

According to another embodiment, it is possible to form a coating composition containing the diazo compound, the coupler, and the thermosensitive amine producing compound in suspension, and to apply this composition to a suitable support material, e.g. paper, such as glassine paper, as a single coat.

As suitable binders by which the thermosensitive amine producing compound can be held in potentially reactive association with a surrounding underlying or supercoated diazo-type composition are mentioned e.g.: polyvinyl ethyl ether, polyvinyl acetate, polymethyl methacrylate, polyvinylidene chloride, polyvinyl alcohol, gelatin, ethyl-cellulose, methylcellulose, and other synthetic and natural resins wherein the amine-producing compound either can be dissolved or dispersed.

Since the reactivity of different diazo-type systems will be different, different amounts of amine-producing compounds as described above will be used. In each particular case the amount required for any given system may easily be determined experimentally.

According to a preferred embodiment a diazo-oxide compound e.g. a naphthalene-diazo-oxide is coated in a one-layer system together with a binder or binder composition, a coupling agent and the heat-sensitive amine progenitor.

Such "one-layer recording material" does not show any premature coupling in the absence of light.

Particularly suited for that purpose are the diazo-oxide compounds listed in the following table 2.

Table 2

1. 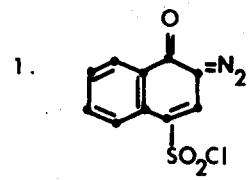

2. 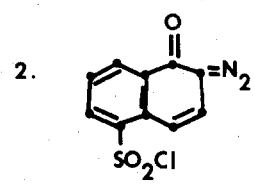

3. 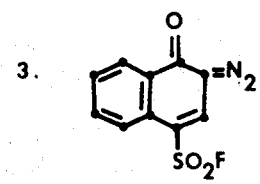

4. 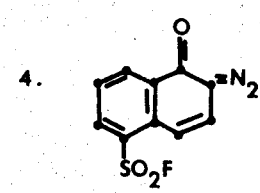

5. 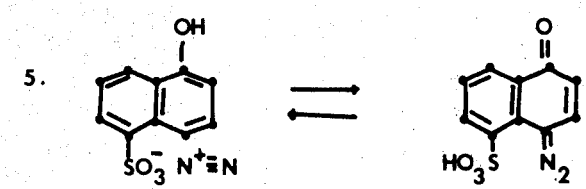

6. 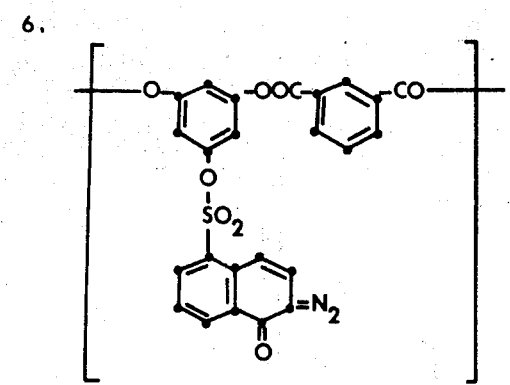

7. 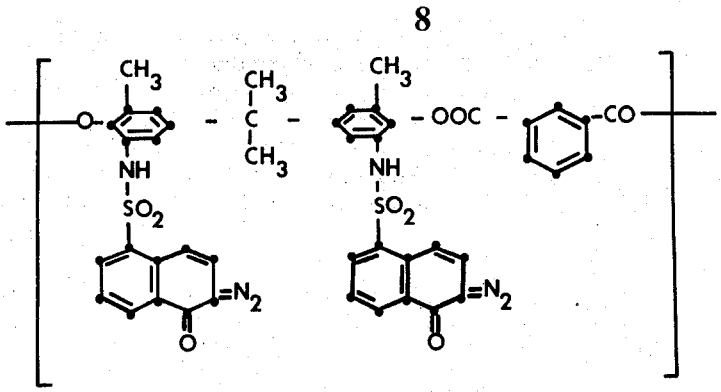
8. 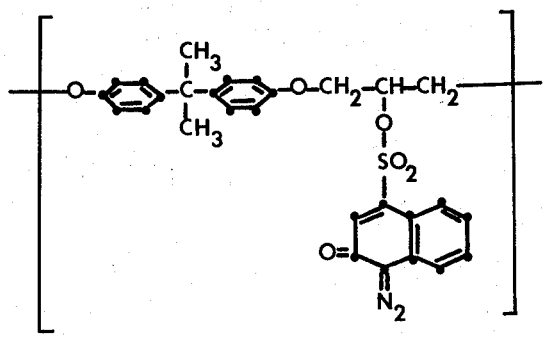
9. 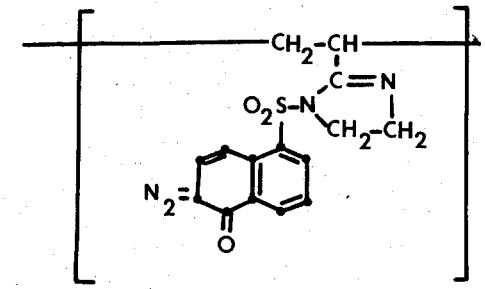
10. 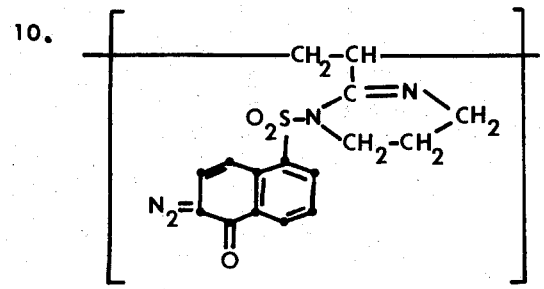
11. 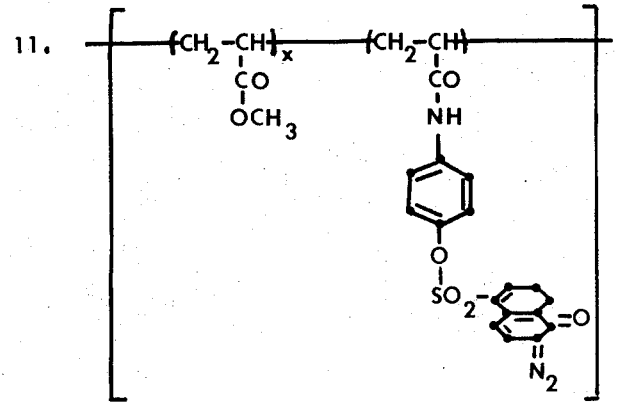

According to another preferred embodiment a recording material containing a diazonium salt is formed by applying the amine progenitor in a layer separate but adjacent, e.g. subjacent, to a layer containing the diazonium compound and coupling agent in the presence of an acid stabilizer. The acid stabilizer has preferably a dissociation constant of $10^{-3}$ or more for adjusting the pH of the layer containing the diazonium salt within a range of 1 to 4, and preferably within the range of 1 to 2.

Typical stabiliziing acids are: citric acid, maleic acid, formic acid, acid phosphates, tartaric acid, succinic acid, boric acid, ascorbic acid, perchloric acid and trichloroacetic acid. The group of stabilizers includes likewise thiourea, zinc chloride, and aluminium sulphate.

Useful couplers for the described diazo compounds are described e.g. in the above mentioned book of J. Kosar and "The Aromatic Diazo Compounds and Their Technical Applications" by K. H. Saunders. The useful couplers may be selected from the class of phenols, and naphthols in which the phenolic hydroxyl group is the only coupling directing group and from the class of compounds containing a reactive methylene or methyl group e.g. the coupling compounds disclosed in the U.S. Pat. Nos. 3,620,740, 3,620,741, 3,676,138, 3,676,140 and 3,676,133.

The following examples illustrate the present invention without, however, limiting it thereto. The ratios and percentages are by weight unless otherwise indicated.

Example 1

Onto an unsubbed polyethylene terephthalate support a heat-developable diazo-type composition was coated from a mixture of the following ingredients:

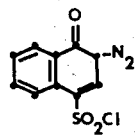  30 mg

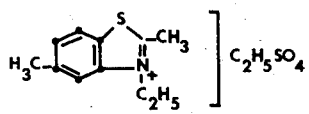  60 mg

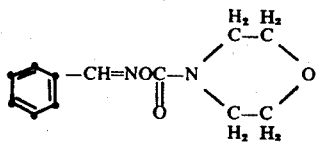  100 mg

| | |
|---|---|
| 10% solution in methylene chloride of polyvinylidene chloride | 5 ml |
| acetone | 5 ml |

The mixture was coated at a wet coating thickness of 0.1 mm.

The dried recording material was exposed through a transparent text original with ultraviolet light in a common diazo-type exposure apparatus and a colour image corresponding with the non-exposed area was developed by a 20 sec heating at 130° C e.g. by leading the exposed recording material through a 3M-Photocopier 179 (trade name).

A positive red-brown image having an optical density 1.00 in the 500-600 nm range was obtained.

Example 2

Onto an unsubbed polyethylene terephthalate support a first layer was applied from the following composition containing a heat-sensitive amine progenitor:

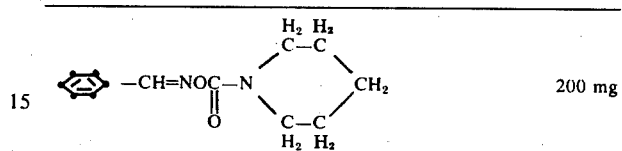  200 mg

| | |
|---|---|
| $CH_2Cl_2$ | 5 ml |
| 10 % solution in methylene chloride of polyvinylidene chloride | 5 ml |

The first coating was applied at a wet coating thickness of 0.1mm. Onto the dried first coating a second coating was applied from the following composition:

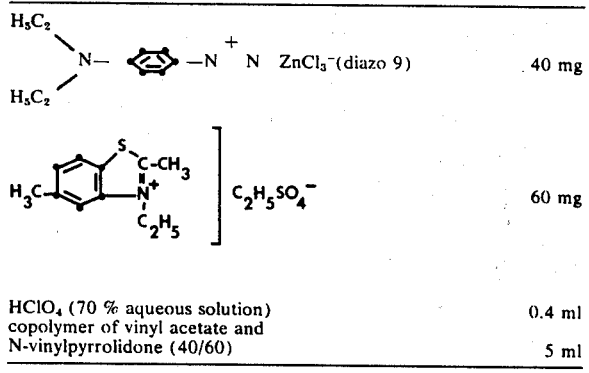

40 mg 60 mg

| | |
|---|---|
| HClO$_4$ (70 % aqueous solution) | 0.4 ml |
| copolymer of vinyl acetate and N-vinylpyrrolidone (40/60) | 5 ml |

The exposure proceeded as described in Example 1, the development was carried out by heating the exposed material for 30 sec. at 140° C.

A positive black image with a density greater than 1.00 was obtained.

Example 3

Onto an unsubbed polyethylene terephthalate support a first layer was coated from the following composition:

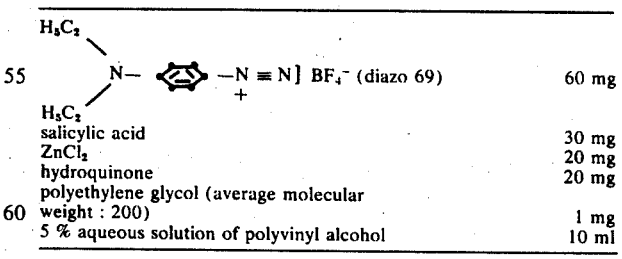  60 mg

| | |
|---|---|
| salicylic acid | 30 mg |
| ZnCl$_2$ | 20 mg |
| hydroquinone | 20 mg |
| polyethylene glycol (average molecular weight : 200) | 1 mg |
| 5 % aqueous solution of polyvinyl alcohol | 10 ml |

The coating was applied at a wet coating thickness of 0.032 mm.

Onto the dried first coating a second coating was applied at a wet coating thickness of 0.08 mm from the following composition:

|   |   |
|---|---|
| [benzothiazolium structure] $C_2H_5SO_4^-$ | 72 mg |
| [Ph-CH=N-O-C(=O)-N(morpholine) structure]<br>5 % solution in methylene chloride of polyvinylidene chloride | 200 mg<br>10 ml |

The exposure proceeded as described in Example 1, the development was carried out by heating the exposed material for 30 sec at 140° C.

A positive blue image with a density greater than 1.00 was obtained.

Example 4

Onto an unsubbed polyethylene terephthalate support a layer was coated at a wet coating thickness of 0.016 mm.

|   |   |
|---|---|
| $H_3C\!-\!N(\!-\!C_6H_4\!-\!N=N\!-\!O_2S\!-\!C_6H_4\!-\!CH_3)\!-\!CH_3$ | 5 mg |
| [benzothiazolium structure] $C_2H_5SO_4^-$ | 30 mg |
| [Ph-CH=N-O-C(=O)-N(morpholine) structure] | 100 mg |

The exposure proceeded as described in Example 1, the development was carried out by heating the exposed material for 30 sec at 140° C.

A positive blue image with density 0.7 was obtained.

Example 5

Onto an unsubbed polyethylene terephthalate support a first layer was coated at a wet coating thickness of 0.032 mm.

|   |   |
|---|---|
| 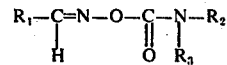 $(H_5C_2)_2N\!-\!C_6H_4\!-\!N\!\equiv\!N]\ BF_4^-$ (diazo 69) | 60 mg |
| $Cl_3C\text{-}COOH$ | 30 mg |
| polyethylene glycol (average molecular weight : 200) | 1 mg |
| hydroquinone | 20 mg |
| $ZnCl_2$ | 20 mg |
| 10 % aqueous solution of polyvinyl alcohol | 5 ml |
| water | 5 ml |

Onto the dried first coating a second coating was applied at a wet coating thickness of 0.1 mm from the following composition:

|   |   |
|---|---|
| phloroglucinol | 60 mg |
| [Ph-CH=N-O-C(=O)-N(morpholine) structure]<br>5 % by weight solution in methylene chloride of polyvinylidene chloride | 200 mg<br>10 ml |

The exposure proceeded as described in Example 1, the development was carried out by heating the exposed material for 30 sec. at 140° C.

A red positive image with a density equal to 1.00 in the 500 to 600 nm range was obtained.

We claim:

1. A diazo recording process which comprises the steps of (1) information-wise exposing to ultra-violet light and (2) overall heating a recording material comprising a compound yielding an amine on heating, an ultra-violet light-sensitive diazo compound and a coupling component capable of yielding a dyestuff by reaction with unaffected diazo compound when heating said material and wherein the compound yielding an amine on heating corresponds with the following general formula:

$$R_1\!-\!\underset{H}{C}\!=\!N\!-\!O\!-\!\underset{O}{\overset{\|}{C}}\!-\!\underset{R_3}{N}\!-\!R_2$$

in which:
R₁ represents
 1. an aliphatic group or a cycloaliphatic group,
 2. an aryl group,
 3. a heterocyclic group, or
 4. an acyl group,
R₂ represents an aliphatic group or a cycloaliphatic group,
R₃ represents
 1. hydrogen,
 2. an aliphatic group including a cycloaliphatic group, or
R₃ and R₂ form together part of a heterocyclic ring.

2. A process according to claim 1, wherein R₂ and R₃ form together part of a saturated heterocyclic ring.

3. A process according to claim 1, wherein R₁ represents phenyl.

4. A process according to claim 2, wherein R₂ and R₃ together represent the necessary atoms to close a piperidine or morpholine nucleus.

5. A process according to claim 1, wherein the diazo compound is a diazonium salt.

6. A process according to claim 1, wherein the diazo compound is an aromatic diazo-oxide.

7. A process according to claim 1, wherein the diazo compound is a diazo sulphone.

8. A recording material containing in or on a support a diazo compound and coupling agent in operative relationship with a thermosensitive amine progenitor corresponding to the following general formula:

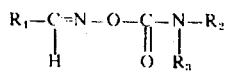

wherein:
R₁ represents
1. an aliphatic group or a cycloaliphatic group,
2. an aryl group,
3. a heterocyclic group, or
4. an acyl group, R₂ represents an aliphatic group or a cycloaliphatic group, R₃ represents
1. hydrogen,
2. an aliphatic group including a cycloaliphatic group, or R₃ and R₂ together part of a heterocyclic ring, and R₄ represents hydrogen.

9. A recording material according to claim 8, wherein R₁ represents phenyl.

10. A recording material according to claim 8, wherein R₂ and R₃ together form part of a piperidine or morpholine nucleus.

11. A recording material according to claim 8, wherein said amine progenitor is present in a binder medium.

12. A recording material according to claim 8, wherein the thermosensitive amine progenitor is present in admixture with said diazo compound and a phenol, naphthol and/or active methylene type coupler.

13. A recording material according to claim 8, wherein the diazo compound is a diazonium salt.

14. A recording material according to claim 8, wherein the diazo compound is an aromatic diazo-oxide.

15. A recording material according to claim 8, wherein the diazo compound is a diazo sulphone.

16. A recording material according to claim 14, wherein the diazo-oxide is present in a one-layer system together with a binder or binder composition, a coupling agent and the heat-sensitive amine progenitor.

17. A recording material according to claim 13, wherein the amine progenitor is present in an intermediate layer between a support and a layer containing the diazonium compound and a coupling agent therefor.

* * * * *

UNITED STATES PATENT AND TRADEMARK OFFICE
CERTIFICATE OF CORRECTION

PATENT NO. : 3,985,562
DATED : October 12, 1976
INVENTOR(S) : Ludovicus Maria Mertens et al It is certified that error appears in the above-identified patent and that said Letters Patent are hereby corrected as shown below:

Column 13, line 18 (claim 8, second line from the end), -- form -- should be inserted after "$R_2$"; and the comma after "ring" should be changed to a period and the remainder of the claim cancelled.

Signed and Sealed this

Fourteenth Day of December 1976

[SEAL]

Attest:

RUTH C. MASON
*Attesting Officer*

C. MARSHALL DANN
*Commissioner of Patents and Trademarks*